United States Patent [19]

Ferrand et al.

[11] 4,163,852

[45] Aug. 7, 1979

[54] PROCESS FOR THE PREPARATION OF TETRAHYDRO-THIENO[3,2-c]- AND [2,3-c]PYRIDINE DERIVATIVES

[75] Inventors: Gérard Ferrand; Jean-Pierre Maffrand, both of Toulouse, France

[73] Assignee: Parcor, Paris, France

[21] Appl. No.: 860,188

[22] Filed: Dec. 13, 1977

Related U.S. Application Data

[63] Continuation of Ser. No. 689,928, May 25, 1976, abandoned.

[30] Foreign Application Priority Data

Jul. 9, 1975 [FR] France ................................ 75 21549

[51] Int. Cl.$^2$ ............................................. C07D 495/04
[52] U.S. Cl. .................................... 546/114; 424/256
[58] Field of Search .................. 260/294.8 C; 546/114

[56] References Cited

U.S. PATENT DOCUMENTS

| | | | |
|---|---|---|---|
| 3,969,358 | 7/1976 | Amsalem | 260/294.8 C |
| 4,051,141 | 9/1977 | Castaigne | 260/294.8 C |
| 4,065,460 | 12/1977 | Heymes et al. | 260/294.8 C |

*Primary Examiner*—Alan L. Rotman
*Attorney, Agent, or Firm*—Young & Thompson

[57] ABSTRACT

This invention relates to a process for the preparation of tetrahydro-thieno[3,2-c]pyridine derivatives of the formula

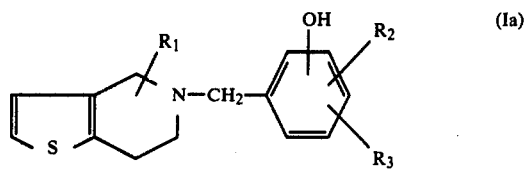

and their isomeric tetrahydro-thieno[2,3-c]pyridine derivatives in which $R_1$ represents hydrogen, a lower alkyl or alkoxy radical, an aryl radical or an aralkyl radical; $R_2$ and $R_3$ represent hydrogen, halogen, a lower alkyl or alkoxy group, a di(loweralkyl)amino, nitro, cyano or acetamido group or, together with the phenyl nucleus to which they are attached, form a polycyclic aromatic ring, comprising reacting a tetrahydro-thieno[3,2-c]pyridine derivative of the formula:

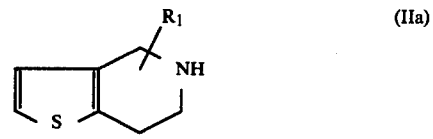

or a derivative of its isomer, tetrahydro[2,3-c]pyridine, with formaldehyde H-CHO and a phenol of the formula:

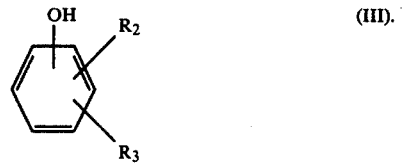

3 Claims, No Drawings

PROCESS FOR THE PREPARATION OF TETRAHYDRO-THIENO[3,2-c]- AND [2,3-c]PYRIDINE DERIVATIVES

This is a continuation, of application Ser. No. 689,928, filed May 25, 1976 now abandoned.

This invention relates to a new process for the preparation of tetrahydro-thieno[3,2-c]pyridine derivatives of the formula:

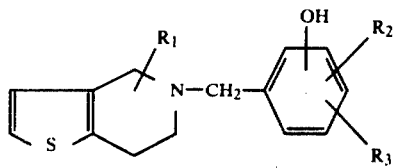

and their isomers, tetrahydrothieno[2,3-c]pyridine derivatives of the formula:

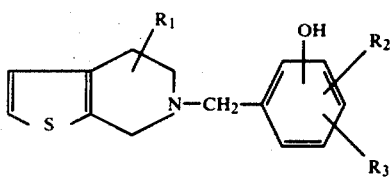

in which the hydroxyl group OH is at 2- or 4-position; $R_1$ represents hydrogen, a lower alkyl or alkoxy radical, an aryl radical or an aralkyl radical; $R_2$ and $R_3$ represent each hydrogen, halogen, a lower alkyl or alkoxy radical, a di-(loweralkyl)amino, nitro, cyano or acetamido radical or, together with the phenyl nucleus to which they are attached, form naphthyl, $R_2$ and $R_3$ being at 3-, 4-, 5- or 6-position when OH is at 2-position and being at 3- and 5-positions and other than hydrogen when OH is at 4-position.

Said compounds possess valuable therapeutic properties and, in addition, are useful intermediates in the preparation of derivatives used both in the chemical and pharmaceutical industries. Specifically, they have anti-inflammatory action and an inhibiting action on blood platelet aggregation. In addition, the [3,2-c] derivatives have peripheral and cerebral vasodilatator activity; while the [2,3-c] derivatives have antiarhythmic activity.

4,5,6,7-Tetrahydro-thieno[3,2-c]pyridine derivatives have already been described, together with a process for their preparation, in French Patent application No. 73 03 503, which corresponds to U.S. Pat. 4,051,141.

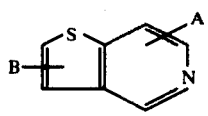

in which the radicals A and B represent each at least an atom or group selected from hydrogen, halogen, lower alkyl, lower alkoxy, nitro and amino, with a halide of the formula Hal-R in which Hal represents a halogen atom and R represents an optionally substituted alkyl, aryl or aralkyl radical, to give a pyridinium salt of the formula:

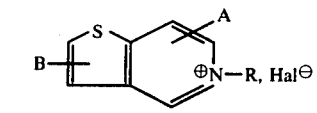

and subsequently hydrogenating said pyridinium salt to give a derivative of the formula (I):

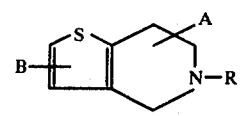

4,5,6,7-Tetrahydro-thieno[2,3-c]pyridine derivatives have also been prepared by an analogous process (French Patent application No. 75 20 241, which corresponds to U.S. Pat. No. 4,075,340).

This process, however, is expensive and delicate in that it requires numerous difficult procedures.

In addition, use of this preparation process makes it difficult to obtain derivatives having on the nitrogen atom a benzyl radical carrying a hydroxyl group at 2- or 4-position. Indeed, to obtain derivatives of such type according to said process, it is necessary to proceed via the methoxylated derivative which is subsequently hydrolyzed.

Therefore, the object of the present invention is to provide a simple process for the preparation, in good yields, of derivatives of the formula (Ia) or their isomers of the formula (Ib) in which the phenyl nucleus carries a hydroxy group at 2- or 4-position.

The process of this invention comprises reacting a tetrahydrothieno[3,2-c]pyridine derivative of the formula:

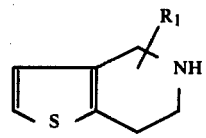

or a derivative of its isomer, tetrahydro[2,3-c]pyridine, of the formula:

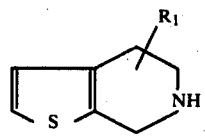

in which $R_1$ has the above-described meanings, with formaldehyde H-CHO and a phenol of the formula

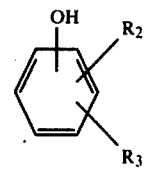

in which $R_2$ and $R_3$ have the above-defined meanings, to give the desired derivative of the formula (Ia) or (Ib).

The (Mannich type) reaction occurs at one of the ortho-positions of the phenol, when it is free. When both ortho-positions are occupied, the reaction occurs at the para-position.

Thus, in the case of phenols in which at least one of the positions ortho to OH is free, the Mannich reaction occurs at said free ortho-position:

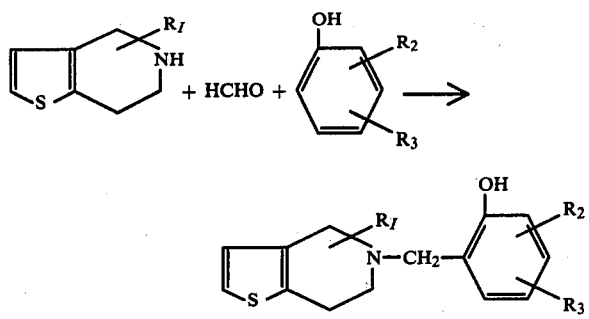

radicals R₂ and R₃ occupying optionally 3-, 4-, 5- or 6-positions in the derivative of the formula (Ia) or (Ib).

The same reaction occurs with unsubstituted phenol, and with polycyclic phenols such as β-naphthol, for example.

In the case of phenols carrying both substituents R₂ and R₃ at ortho-position to the OH radical, the reaction occurs at para-position:

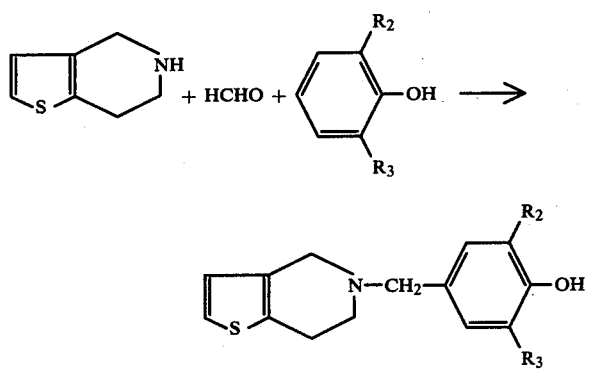

The condensation reaction of this invention is advantageously conducted within a medium consisting of an organic solvent such as ethanol, propanol or dioxan. The reaction is advantageously effected in the hot, at a temperature between 50° C. and the boiling temperature of the solvent used, best results being obtained at temperatures of about 80° C.

It is preferred to effect the reaction wth constant stirring, during a period of time of 2–20 hours.

Formaldehyde or its different polymerization products, such as polyoxymethylene, may be used for the reaction.

Purification of the desired derivative is effected either by recrystallization from an organic solvent, or after conversion to a salt, by washing, drying and optionally recrystallization from an organic solvent.

The following non-limiting Examples are given to illustrate the present invention.

EXAMPLE 1

Preparation of 5-(3,5-dimethyl-4-hydroxy-benzyl)-4,5,6,7-tetrahydro-thieno[3,2-c]pyridine A mixture of 4,5,6,7-tetrahydro-thieno[3,2-c]pyridine (6.1 g; 44 mmoles), 2,6-dimethyl-phenol (5.4 g; 44 mmoles), polyoxymethylene (2.7 g; 90 mmoles) and dioxan (50 cc) is stirred at 80° C. during 3 hours. After concentration in vacuo, the residue is recrystallized from ethanol-isopropanol (M.p.=158° C.; yield: 48%).

EXAMPLE 2

Preparation of 5-(2-hydroxy-5-nitro-benzyl)-6-methyl-4,5,6,7-tetrahydro-thieno[3,2-c]pyridine A mixture of 6-methyl-4,5,6,7-tetrahydro-thieno[3,2-c]pyridine (6.3 g; 41 mmoles), p-nitro-phenol (5.7 g; 41 mmoles), polyoxymethylene (2.5 g; 83 mmoles) and dioxan (50 cc) is stirred at 80° C. during 4 hours. After concentration in vacuo, the residue is dissolved in ether and then treated with 0.5 equivalent oxalic acid in ethanol solution. The resulting semi-oxalate is filtered, washed with boiling methanol-water (1:3), filtered again and dried (M.p.=214° C.; yield: 27%).

EXAMPLE 3

Preparation of 6-(2-hydroxy-5-chloro-benzyl)-7-methyl-4,5,6,7-tetrahydro-thieno[2,3-c]pyridine A mixture of 7-methyl-4,5,6,7-tetrahydro-thieno[2,3-c]pyridine (6.0 g; 39.2 mmoles), p-chlorophenol (5.05 g; 39.2 mmoles), polyoxymethylene (2.36 g; 78.5 mmoles) and dioxan (70 cc) is stirred at 80° C. during 15 hours. After concentration in vacuo, the residue is taken up into 2N hydrochloric acid. The aqueous phase is extracted with ether, made basic with concentrated ammonia and again extracted with methylene chloride. The organic extracts are washed with water, dried over sodium sulfate and concentrated in vacuo. The residue is treated with 0.5 equivalent oxalic acid in ethanol solution. The resulting semi-oxalate is filtered and recrystallized from ethanol-dimethyl formamide (M.p.=170° C.; yield: 38%).

EXAMPLE 4

Preparation of 6-(2-hydroxy-5-cyano-benzyl)-4,5,6,7-tetrahydro-thieno[2,3-c]pyridine A mixture of 4,5,6,7-tetrahydro-thieno[2,3-c]pyridine (1 g; 7.2 mmoles), p-cyano-phenol (95% purity; 0.9 g; 7.2 mmoles), polyoxymethylene (0.43 g; 14.4 mmoles) and dioxan (20 cc) is stirred at 80° C. during 4 hours. After concentration in vacuo, the residue is taken up into 2N hydrochloric acid. The aqueous phase is extracted with ether, made basic with concentrated ammonia and again extracted with methylene chloride. The organic extracts are washed with water, dried over sodium sulfate and concentrated in vacuo. The residue is recrystallized from isopropyl ether-isopropanol (M.p. 134° C.; yield: 23%).

Using the procedures described in the preceding Examples, the following compounds are obtained:

EXAMPLE 5

5-(2-Hydroxy-5-methoxy-benzyl)-4,5,6,7-tetrahydro-thieno[3,2-c]pyridine

White crystals; M.p.=90° C.

EXAMPLE 6

5-(2-Hydroxy-5-nitro-benzyl)-4,5,6,7-tetrahydro-thieno[3,2-c]pyridine

Yellow crystals; M.p. M.p.=160° C.

EXAMPLE 7

5-(2-Hydroxy-3-methoxy-benzyl)-4,5,6,7-tetrahydro-thieno[3,2-c]pyridine

White crystals; M.p.=84° C.

EXAMPLE 8

5-(5-Chloro-2-hydroxy-benzyl)-4,5,6,7-tetrahydro-thieno[3,2-c]pyridine
White crystals; M.p.=82°-85° C.

EXAMPLE 9

5-(5-Chloro-2-hydroxy-benzyl)-6-methyl-4,5,6,7-tetrahydro-thieno[3,2-c]pyridine, semi-oxalate
White crystals; M.p.=200° C.

EXAMPLE 10

5-(5-Fluoro-2-hydroxy-benzyl)-4,5,6,7-tetrahydro-thieno[3,2-c]pyridine
Pale yellow crystals; M.p.=92° C.

EXAMPLE 11

5-o-Hydroxybenzyl-4,5,6,7-tetrahydro-thieno[3,2-c]pyridine, semi-oxalate
White crystals; M.p.=216° C.

EXAMPLE 12

5-(2-Hydroxy-3-methyl-benzyl)-4,5,6,7-tetrahydro-thieno[3,2-c]pyridine semi-oxalate, semi-hydrate
White crystals; M.p.=198° C.

EXAMPLE 13

5-(3-Acetamido-2-hydroxy-benzyl)-4,5,6,7-thieno[3,2-c]pyridine
White crystals; M.p.=154° C.

EXAMPLE 14

6-(5-Chloro-2-hydroxy-benzyl)-4,5,6,7-tetrahydro-thieno[2,3-c]pyridine
White crystals; M.p.=222° C.

EXAMPLE 15

6-(3,4,-Dichloro-2-hydroxy-benzyl)-4,5,6,7-tetrahydro-thieno[2,3-c]pyridine
White crystals; M.p.=153° C.

EXAMPLE 16

6-(2-Hydroxy-5-nitro-benzyl)-4,5,6,7-tetrahydro-thieno[2,3-c]pyridine
Yellow crystals; M.p.=159° C.

EXAMPLE 17

6-(3,5-Dimethyl-4-hydroxy-benzyl)-4,5,6,7-tetrahydro-thieno[2,3-c]pyridine
Ivory crystals; M.p.=118° C.

EXAMPLE 18

6-(2-Hydroxy-3-isopropyl-benzyl)-4,5,6,7-tetrahydro-thieno[2,3-c]pyridine
Very pale yellow crystals; M.p.=101° C.

EXAMPLE 19

6-(2-Hydroxy-5-methyl-benzyl)-4,5,6,7-tetrahydro-thieno[2,3-c]pyridine, semi-oxalate, semi-hydrate
Very pale yellow crystals; M.p.=196° C.

EXAMPLE 20

6-(4-dimethylamino-2-hydroxy-benzyl)-4,5,6,7-tetrahydro-thieno[2,3-c]pyridine
Pink crystals; M.p.=140° C.

EXAMPLE 21

6-o-Hydroxybenzyl-4,5,6,7-tetrahydro-thieno[2,3-c]pyridine
Beige crystals; M.p.=98° C.

EXAMPLE 22

6-(1-β-Hydroxynaphthyl-methyl)-4,5,6,7-tetrahydro-thieno[3,2-c]pyridine
Pale yellow crystals; M.p.=150° C.

EXAMPLE 23

5-(3,5-Dichloro-4-hydroxy-benzyl)-4,5,6,7-tetrahydro-thieno[3,2-c]pyridine
White crystals; M.p.=170° C.

Having now described our invention what we claim as new and desire to secure by Letters Patent is:

1. Process for the preparation of derivatives selected from the group consisting of the tetrahydro-thieno(3,2-c)pyridine derivatives of the formula:

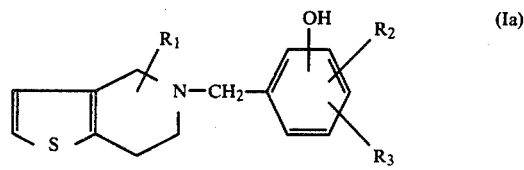

and their isomeric pyridine derivatives of the formula:

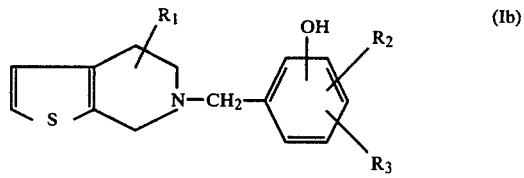

in which the hydroxyl radical is at the 2-position; $R_1$ is hydrogen; $R_2$ is hydrogen; and $R_3$ is selected from the group consisting of hydrogen, halogen, lower alkyl, lower alkoxy and nitro; comprising reacting in an organic solvent at a temperature between 50° C. and the boiling temperature of the solvent a derivative selected from the group consisting of the tetrahydro-thieno(3,2-c)pyridine derivatives of the formula:

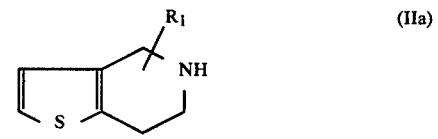

and their isomeric tetrahydro-thieno(2,3-c)pyridine derivatives of the formula:

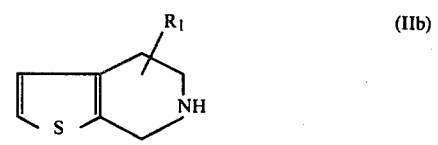

in which $R_1$ is hydrogen, with formaldehyde and a phenol of the formula:

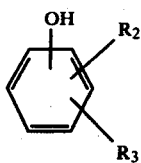

(III)

in which $R_2$ and $R_3$ have the above-defined meanings, to give the desired derivative selected from the pyridine derivatives of the formulae (Ia) and (Ib).

2. Process as claimed in claim 1, wherein said organic solvent is selected from the group consisting of ethanol, propanol and dioxan.

3. Process as claimed in claim 1, wherein the reaction is effected with stirring, during a period of time of 2–20 hours.

* * * * *